US011983959B2

(12) United States Patent
Martinez

(10) Patent No.: US 11,983,959 B2
(45) Date of Patent: May 14, 2024

(54) SECURING DATA OF OBJECTS IN A LABORATORY ENVIRONMENT

(71) Applicant: Beckman Coulter, Inc., Brea, CA (US)

(72) Inventor: Charles Martinez, Yorba Linda, CA (US)

(73) Assignee: Beckman Coulter, Inc., Brea, CA (US)

(*) Notice: Subject to any disclaimer, the term of this patent is extended or adjusted under 35 U.S.C. 154(b) by 500 days.

(21) Appl. No.: 17/289,345

(22) PCT Filed: Apr. 17, 2020

(86) PCT No.: PCT/US2020/028652
§ 371 (c)(1),
(2) Date: Apr. 28, 2021

(87) PCT Pub. No.: WO2020/214897
PCT Pub. Date: Oct. 22, 2020

(65) Prior Publication Data
US 2021/0397821 A1 Dec. 23, 2021

Related U.S. Application Data

(60) Provisional application No. 62/835,833, filed on Apr. 18, 2019.

(51) Int. Cl.
*G06K 9/00* (2022.01)
*G06N 20/00* (2019.01)
(Continued)

(52) U.S. Cl.
CPC ........... *G06V 40/172* (2022.01); *G06N 20/00* (2019.01); *G06V 10/25* (2022.01); *G06V 40/171* (2022.01); *G16H 10/40* (2018.01); *G06T 19/006* (2013.01)

(58) Field of Classification Search
CPC .... G06V 40/172; G06V 10/25; G06V 40/171; G06N 20/00; G16H 10/40; G06T 19/006; G06T 5/005
See application file for complete search history.

(56) References Cited

U.S. PATENT DOCUMENTS 6,091,546 A 7/2000 Spitzer
6,452,572 B1 9/2002 Fan et al.
(Continued)

FOREIGN PATENT DOCUMENTS

CN 201054051 Y 4/2008
CN 101258436 A 9/2008
(Continued)

OTHER PUBLICATIONS

International Search Report and Written Opinion dated Feb. 6, 2020, for International Application No. PCT/US2019/056473, 17 pages.
(Continued)

*Primary Examiner* — Xin Jia
(74) *Attorney, Agent, or Firm* — Frost Brown Todd LLP

(57) ABSTRACT

Disclosed subject matter relates to method and system for securing data of objects in a laboratory environment. An image capturing device configured in a laboratory instrument may capture images of plurality of objects in the laboratory environment. A processor in the laboratory instrument may identify one or more objects from the images matching with predefined target objects. The processor may apply virtual masking object on or around the identified objects to prevent exposure of data associated with the identified objects and thus provides data privacy.

19 Claims, 8 Drawing Sheets

(51) Int. Cl.
  *G06V 10/25*   (2022.01)
  *G06V 40/16*   (2022.01)
  *G16H 10/40*   (2018.01)
  *G06T 19/00*   (2011.01)

(56) References Cited

U.S. PATENT DOCUMENTS

| | | |
|---|---|---|
| 7,230,582 B1 | 6/2007 | Dove et al. |
| 7,372,451 B2 | 5/2008 | Dempski et al. |
| 7,447,330 B2 | 11/2008 | Yamasaki |
| 7,511,838 B2 | 3/2009 | Hunter |
| 7,714,895 B2 | 5/2010 | Pretlove et al. |
| 7,715,037 B2 | 5/2010 | Castellani et al. |
| 8,373,618 B2 | 2/2013 | Friedrich et al. |
| 8,430,507 B2 | 4/2013 | Howell et al. |
| 8,434,863 B2 | 5/2013 | Howell et al. |
| 8,471,783 B2 | 6/2013 | Rhodes |
| 8,531,355 B2 | 9/2013 | Maltz |
| 8,531,394 B2 | 9/2013 | Maltz |
| 8,621,362 B2 | 12/2013 | Castellani et al. |
| 8,681,073 B1 | 3/2014 | Robbins et al. |
| 8,681,256 B2 | 3/2014 | Sako et al. |
| 8,832,784 B2 * | 9/2014 | Budko ............... G06F 9/45558 709/227 |
| 8,872,941 B2 | 10/2014 | Asukai et al. |
| 8,934,015 B1 | 1/2015 | Chi et al. |
| 8,982,013 B2 | 3/2015 | Sako et al. |
| 9,122,321 B2 | 9/2015 | Perez et al. |
| 9,128,520 B2 | 9/2015 | Geisner et al. |
| 9,132,342 B2 | 9/2015 | Balachandreswaran et al. |
| 9,153,074 B2 | 10/2015 | Zhou et al. |
| 9,160,993 B1 | 10/2015 | Lish et al. |
| 9,213,163 B2 | 12/2015 | Lewis et al. |
| 9,255,813 B2 | 2/2016 | Liu et al. |
| 9,286,711 B2 | 3/2016 | Geisner et al. |
| 9,323,983 B2 | 4/2016 | Monnerat et al. |
| 9,329,689 B2 | 5/2016 | Osterhout et al. |
| 9,330,313 B2 | 5/2016 | Jung et al. |
| 9,342,751 B2 | 5/2016 | Heo et al. |
| 9,470,894 B2 | 10/2016 | Lee et al. |
| 9,493,125 B2 | 11/2016 | Heo |
| 9,547,184 B2 | 1/2017 | Howell et al. |
| 9,667,855 B2 | 5/2017 | Kim et al. |
| 9,686,466 B1 | 6/2017 | Billinghurst et al. |
| 9,690,099 B2 | 6/2017 | Bar-Zeev et al. |
| 9,706,106 B2 | 7/2017 | Kang et al. |
| 9,710,099 B2 | 7/2017 | Rhee et al. |
| 9,729,767 B2 | 8/2017 | Longbotham et al. |
| 9,729,819 B2 | 8/2017 | Im et al. |
| 9,734,402 B2 | 8/2017 | Jang et al. |
| 9,766,463 B2 | 9/2017 | Border et al. |
| 9,787,890 B2 | 10/2017 | Cho et al. |
| 9,841,599 B2 | 12/2017 | Border |
| 9,860,411 B2 | 1/2018 | Ju et al. |
| 9,866,757 B2 | 1/2018 | He et al. |
| 9,874,998 B2 | 1/2018 | Woo et al. |
| 9,892,561 B2 | 2/2018 | Choukroun et al. |
| 9,904,369 B2 | 2/2018 | Lai et al. |
| 2007/0052672 A1 | 3/2007 | Ritter et al. |
| 2008/0100570 A1 | 5/2008 | Friedrich et al. |
| 2012/0127284 A1 | 5/2012 | Bar-Zeev et al. |
| 2013/0083011 A1 | 4/2013 | Geisner et al. |
| 2013/0083063 A1 | 4/2013 | Geisner et al. |
| 2013/0286163 A1 | 10/2013 | Dror et al. |
| 2014/0085183 A1 | 3/2014 | Na |
| 2014/0380446 A1 | 12/2014 | Niu et al. |
| 2015/0062161 A1 | 3/2015 | Kim et al. |
| 2015/0095041 A1 | 4/2015 | Kim |
| 2015/0235610 A1 | 8/2015 | Miller et al. |
| 2015/0293345 A1 | 10/2015 | Laxhuber et al. |
| 2015/0309316 A1 | 10/2015 | Osterhout et al. |
| 2015/0362729 A1 | 12/2015 | Jang et al. |
| 2016/0034032 A1 | 2/2016 | Jeong |
| 2016/0078449 A1 | 3/2016 | Banerjee |
| 2016/0171780 A1 | 6/2016 | Vardi |
| 2016/0314759 A1 | 10/2016 | Shin et al. |
| 2017/0061212 A1 | 3/2017 | Tanaka et al. |
| 2017/0064207 A1 | 3/2017 | Kim et al. |
| 2017/0064209 A1 | 3/2017 | Cohen et al. |
| 2017/0069135 A1 | 3/2017 | Komaki et al. |
| 2017/0078755 A1 | 3/2017 | Jang et al. |
| 2017/0097802 A1 | 4/2017 | Jeong |
| 2017/0180646 A1 | 6/2017 | Kim et al. |
| 2017/0206509 A1 | 7/2017 | Beyk et al. |
| 2017/0230641 A1 | 8/2017 | Scavezze et al. |
| 2017/0318226 A1 | 11/2017 | Jung et al. |
| 2017/0351920 A1 | 12/2017 | Tanaka et al. |
| 2017/0364162 A1 | 12/2017 | Fujimaki et al. |
| 2018/0011344 A1 | 1/2018 | Calilung et al. |

FOREIGN PATENT DOCUMENTS

| | | |
|---|---|---|
| CN | 102866506 A | 1/2013 |
| CN | 101819334 B | 4/2013 |
| CN | 203399222 U | 1/2014 |
| CN | 102348068 B | 11/2014 |
| CN | 102591016 B | 12/2014 |
| CN | 104182050 A | 12/2014 |
| CN | 204009265 U | 12/2014 |
| CN | 104570399 A | 4/2015 |
| CN | 204390168 U | 6/2015 |
| CN | 104950448 A | 9/2015 |
| CN | 204636276 U | 9/2015 |
| CN | 104090385 B | 11/2015 |
| CN | 105158900 A | 12/2015 |
| CN | 105158927 A | 12/2015 |
| CN | 105158931 A | 12/2015 |
| CN | 105182536 A | 12/2015 |
| CN | 105184276 A | 12/2015 |
| CN | 105204643 A | 12/2015 |
| CN | 105205471 A | 12/2015 |
| CN | 105223706 A | 1/2016 |
| CN | 105224923 A | 1/2016 |
| CN | 105242401 A | 1/2016 |
| CN | 105259657 A | 1/2016 |
| CN | 105353508 A | 2/2016 |
| CN | 105353509 A | 2/2016 |
| CN | 105353510 A | 2/2016 |
| CN | 105355196 A | 2/2016 |
| CN | 105357421 A | 2/2016 |
| CN | 103186922 B | 8/2016 |
| CN | 205427327 U | 8/2016 |
| CN | 106028000 A | 10/2016 |
| CN | 205847478 U | 12/2016 |
| CN | 106291985 A | 1/2017 |
| CN | 205864618 U | 1/2017 |
| CN | 103856590 B | 5/2017 |
| CN | 103529929 B | 6/2017 |
| CN | 104221077 B | 7/2017 |
| CN | 104423038 B | 7/2017 |
| CN | 107272224 A | 10/2017 |
| CN | 206584114 U | 10/2017 |
| CN | 107340853 A | 11/2017 |
| CN | 107680069 A | 2/2018 |
| EP | 2712213 A1 | 3/2014 |
| EP | 2741172 A3 | 8/2015 |
| EP | 3352456 A1 | 7/2018 |
| EP | 3352456 A1 * | 7/2018 ............. G06F 21/31 |
| GB | 2533553 A | 6/2016 |
| JP | 2002-369054 A | 12/2002 |
| JP | 2004-363987 A | 12/2004 |
| JP | 4051702 B2 | 2/2008 |
| JP | 2008-146109 A | 6/2008 |
| JP | 2013-236213 A | 11/2013 |
| JP | 2014-212473 A | 11/2014 |
| JP | 2015-228009 A | 12/2015 |
| JP | 2016-045724 A | 4/2016 |
| JP | 2016-146044 A | 8/2016 |
| JP | 5965410 B2 | 8/2016 |
| JP | 2016-218905 A | 12/2016 |
| JP | 2016-224086 A | 12/2016 |
| JP | 2017-010119 A | 1/2017 |
| JP | 2017-049762 A | 3/2017 |
| JP | 2017-142857 A | 8/2017 |

(56) References Cited

FOREIGN PATENT DOCUMENTS

| | | |
|---|---|---|
| JP | 2017-195552 A | 10/2017 |
| KR | 10-0653303 B1 | 5/2006 |
| KR | 2014-0072651 A | 6/2014 |
| KR | 2014-0146889 A | 12/2014 |
| KR | 2015-0001912 A | 1/2015 |
| KR | 2015-0130767 A | 11/2015 |
| KR | 2016-0066068 A | 6/2016 |
| KR | 2017-0087247 A | 7/2017 |
| WO | WO 2001/095061 A2 | 12/2001 |
| WO | WO 2013/077895 A1 | 5/2013 |
| WO | WO 2014/144918 A3 | 1/2015 |
| WO | WO 2015/032014 A1 | 3/2015 |
| WO | WO 2016/010328 A1 | 1/2016 |
| WO | WO 2016/069588 A1 | 5/2016 |
| WO | WO 2018/014534 A1 | 1/2018 |

OTHER PUBLICATIONS

International Search Report and Written Opinion dated Jun. 12, 2020, for International Application No. PCT/US2020/028652, 8 pages.
U.S. Appl. No. 17/314,247, entitled "Service Glasses with Selective Data Provision," filed May 7, 2021.

* cited by examiner

SECURING DATA OF OBJECTS IN A LABORATORY ENVIRONMENT

PRIORITY

This application is a National Stage Entry of PCT Application No. PCT/US20/28652, entitled "Securing Data of Objects in a Laboratory Environment," filed Apr. 17, 2020, which claims priority to U.S. Provisional Application No. 62/835,833, entitled "Securing Data of Objects in a Laboratory Environment," filed Apr. 18, 2019, the disclosures of which are incorporated by reference herein.

This is related to, and claims the benefit of, previously filed provisional application 62/835,833, filed in the United States on Apr. 18, 2019 and titled securing data of objects in a laboratory environment. The disclosure of that application is hereby incorporated by reference in its entirety.

TECHNICAL FIELD

This disclosure relates generally to instruments.

BACKGROUND

Generally, laboratory environment may be associated with laboratory instruments which perform various operations. The laboratory environment may also include personnel operating the laboratory instruments. Normally, various operations of the laboratory instruments may be captured in the form of images and videos by an image capturing device such as a camera associated with the laboratory instrument. Due to this, the image capturing device may capture images and videos of objects present in proximity of the laboratory instruments along with the images and videos of operations of the laboratory instruments. The objects present in proximity of the laboratory instrument may include face region of one or more personnel in the laboratory environment, one or more equipment in the laboratory environment such as standalone analyzers, table top analyzers, one or more regions of the equipments such as consoles or display region. Usually, capturing images and videos of such objects may carry a risk of exposing information which may be confidential such as personal information of a user proximal to the laboratory instrument or information associated with one or more objects, thereby compromising on data privacy/security.

The present disclosure provides a method, a system and a laboratory instrument to secure data associated with the objects in the laboratory environment thereby overcoming the current disadvantage.

The information disclosed in this background of the disclosure section is only for enhancement of understanding of the general background of the disclosure and should not be taken as an acknowledgement or any form of suggestion that this information forms prior art already known to a person skilled in the art

SUMMARY

One or more shortcomings of the prior art may be overcome, and additional advantages may be provided through embodiments of the present disclosure. Additional features and advantages may be realized through the techniques of the present disclosure. Other embodiments and aspects of the disclosure are described in detail herein and are considered a part of the claimed disclosure.

Embodiments of the present disclosure relate to a method for securing data associated with objects captured in a laboratory environment. In one embodiment, the method includes receiving images of a plurality of objects in the laboratory environment. In a further embodiment, the method includes identifying one or more objects from the images which matches predefined target images. The predefined target objects may include secure data. The method further includes applying a virtual masking object on and around the one or more objects matching with the predefined target objects for securing data associated with the one or more objects. In some embodiment, the virtual masking object is applied on the one or more objects when the identified one or more objects are one of face region of a user in a laboratory environment or ID card of the user which consist of confidential data of the user. In some embodiment, the virtual masking object is applied around the one or more objects when the identified one or more objects are equipments or region of equipments which match the predefined target objects. The virtual masking object is applied at a predefined distance from a laboratory instrument configured with an image capturing device for capturing the images.

The foregoing summary is only illustrative in nature and is not intended to be in any way limiting on the embodiments disclosed herein. In addition to the illustrative aspects, embodiments, and features described above, further aspects, embodiments, and features will become apparent by reference to the drawings and the following detailed description.

BRIEF DESCRIPTION OF THE ACCOMPANYING DIAGRAMS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same reference numbers are used throughout the figures to reference like features and components. Some embodiments of system and/or methods in accordance with embodiments of the present subject matter are now described, by way of example only, and with reference to the accompanying figures, in which:

Figure 1A:
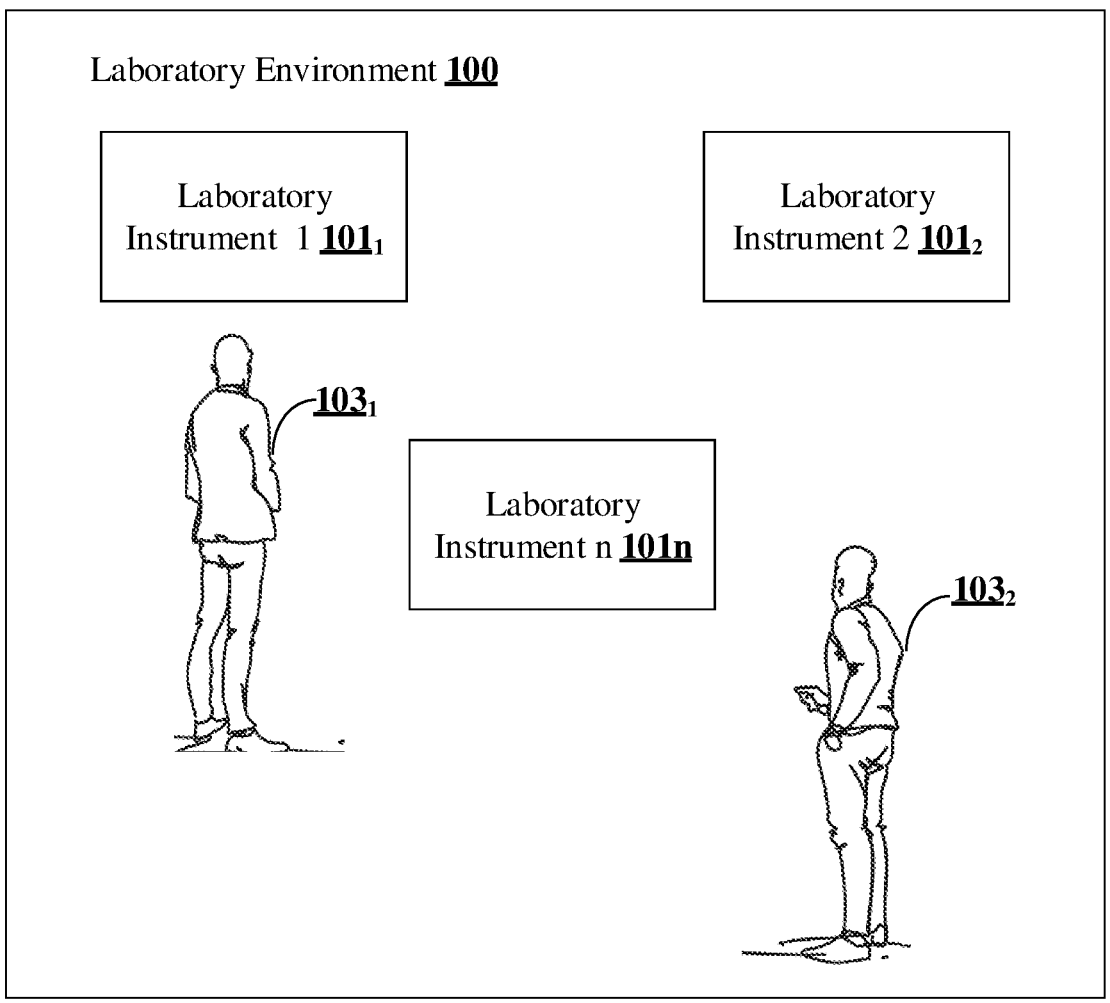
FIG. 1A illustrates an exemplary laboratory environment in accordance with embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the teachings of this disclosure, and it is to be understood that other embodiments may be utilized and that changes may be made without departing from the scope of the present disclosure. The following description is, therefore, not to be taken in a limiting sense. A description of an embodiment with several components in communication with each other does not imply that all such components are required. On the contrary a variety of optional components are described to illustrate the wide variety of possible embodiments of the invention.

In the present document, the word "exemplary" is used herein to mean "serving as an example, instance, or illustration." Any embodiment or implementation of the present subject matter described herein as "exemplary" is not necessarily construed to be as preferred or advantageous over other embodiments that may be disclosed.

While the disclosure is susceptible to various modifications and alternative forms, specific embodiment thereof have been illustrated by way of example in the drawings and will be described in detail below. It should be understood, however that this is not intended to limit the disclosure to the forms disclosed, but on the contrary, the disclosure is to cover all modifications, equivalents, and alternative falling within the scope of the disclosure.

The terms "comprises", "comprising", "includes" or any other variations thereof, are intended to cover a non-exclusive inclusion, such that a setup, device or method that includes a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method. Also, the words "comprising," "having," "containing," and "including," and other similar forms are intended to be equivalent in meaning and be open-ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

According to one embodiment, a method of securing data associated with objects captured in a specific environment may be provided. In an example embodiment, such a specific environment may be a laboratory environment. Such a method may comprise receiving images of a plurality of objects, wherein the plurality of objects may be associated with a device. Such a method may comprise identifying, from the images, one or more objects matching with predefined target objects. Such a method may comprise applying a virtual masking object on the one or more objects matching with the predefined target objects for securing data associated with the one or more matching objects.

According to a further embodiment, a method such as described in the preceding paragraph may be configured to allow a user to mark the plurality of objects dynamically in real time. According to a further embodiment, a method such as described in the preceding paragraph may be provided in which applying the virtual masking object around the one or more objects may comprise identifying a predefined distance around an equipment in the specific environment comprising an image capturing device configured to capture the image of the plurality of objects in the specific environment. In such methods, applying the virtual masking object around the one or more objects may also comprise applying the virtual masking object at the predefined distance from the image capturing device. According to a further embodiment, a method such as described in the preceding paragraph may be provided in which applying the virtual masking object around the one or more objects comprises marking in real time by a user a predefined distance around an equipment in the specific environment comprising an image capturing device configured to capture the image of the plurality of objects in the specific environment. In such methods, applying the virtual masking object around the one or more objects may also comprise applying the virtual masking object at the predefined distance from the image capturing device.

According to a further embodiment, a method such as described in any of the preceding two paragraphs may be provided in which the one or more objects may comprise at least one of a face region of one or more personnel in the specific environment or a region selected in real time by the user, identification card of the one or more personnel in the specific environment, one or more equipment in the specific environment, and one or more regions of one or more equipment.

According to a further embodiment, a method such as described in any of the preceding three paragraphs may be provided in which the one or more objects matching with the predefined target objects may be identified based on processing of the one or more objects using a machine learning technique.

According to further embodiment, a method such as described in any of the preceding four paragraphs may be provided in which an image of the plurality of objects in the laboratory environment may be a still image or a video.

According to a further embodiment, a method such as described in any of the preceding five paragraphs may be provided wherein the specific environment is a laboratory environment, and where in the device is a laboratory instrument.

According to a further embodiment, a system for securing data associated with objects captured in a laboratory environment may be provided. Such a system may comprise a processor and a memory unit communicatively coupled to the processor and storing processor-executable instructions which, on execution, cause the processor to perform a method as described in the context of any of the preceding six paragraphs. According to another embodiment, a laboratory instrument may be provided which comprises at least one image capturing device to capture an image of a plurality of objects in a laboratory environment and a processor configured to perform a method such as described in the context of any of the preceding six paragraphs.

Embodiments disclosed herein may include a method, system and a laboratory instrument (generally referred as diagnostic instruments) for securing data associated with objects in a laboratory environment. In some embodiments, the objects may include, but are not limited to, equipment such as laboratory instruments, one or more personnel in the laboratory environment and one or more regions of the equipments. In some embodiments the data may be personal information associated with the one or more personnel and confidential data associated with the equipments. In some embodiments, the laboratory instrument may include, but are not limited to, a diagnostic instrument and a non-diagnostic instrument. In a further embodiment, the laboratory instrument may include health care related instruments. In some embodiment, the phrase "one or more personnel" and the word "personnel" may be alternatively used. The laboratory instrument may be associated with one or more devices to perform at least one operation of the laboratory instrument. In some embodiments, at least one image capturing device and a processor may be coupled to the laboratory instrument. In some embodiments, the phrase "at least one image capturing device" and the word "image capturing device/s" may be alternatively used. In some embodiments, the image capturing device(s) may be configured to capture at least one of images and videos during operations of the laboratory instrument. In some embodiments, the image capturing device(s) may be stationary having a fixed Field of View (FOV). In some other embodiments, the image capturing device(s) may be movable having a varying FOVs. In some embodiments, the image capturing device associated with the laboratory instrument may capture images of the plurality of objects in the laboratory environment. In certain other embodiments, the processor may receive the captured image. Upon receiving the captured image, the processor may identify one or more objects matching with predefined target objects. In some embodiments, the predefined target objects may be face region of one or more personnel in the laboratory instrument. In some other embodiments, the predefined target object may be equipments such as table-top analyzers and stand alone analyzers. In yet some other embodiments, the phrase "one or more equipment" and the word "equipments" may be alternatively used. In some other embodiments, the predefined target object may be one or more regions of the one or more equipment such as a console screen. In some other embodiment, a user may be allowed to mark a region of interest in real time, defining the predefined target object.

In some embodiments, the processor may apply a virtual masking object on or/and around the identified one or more objects to secure data associated with the identified one or more objects. In some other embodiments, if the identified object is face region of the one or more personnel in the laboratory environment or identification (ID) card of the one or more personnel, the virtual masking object may include, but not limited to, an emoticon may be applied on the identified face region or the identified ID card. In some embodiments, if the identified one or more objects are one or more equipment or one or more regions of the one or more equipment such as a table top analyzer, standalone analyzer, the processor may apply the virtual masking object around the identified one or more objects. In some embodiments, the virtual masking object may be applied at a predefined distance from the laboratory instrument comprising the image capturing device. In some embodiments, the virtual masking object may include, but is not limited to, augmented reality based curtain panel. In some embodiments, the virtual masking object may be applied to mask the identified objects and hence prevents exposure of the data related to the identified objects to the outside environment. In some embodiment, the outside environment may be a remote server associated with the one or more equipment in the laboratory environment. In some other embodiment, the outside environment may be any other environment external to the laboratory environment.

Reference is now made to FIG. 1A, which illustrates an exemplary laboratory environment in accordance with embodiments of the present disclosure.

The laboratory environment 100 may include one or more equipments such as one or more laboratory instruments (laboratory instrument 1 101$_1$ to laboratory instrument 101$n$, collectively referred as laboratory instruments 101) and one or more users or one or more personnel's (collectively referred as users/user 103) in the laboratory environment 100 for operating or viewing operations of the laboratory instruments 101. As an example, the laboratory instruments 101 may be a diagnostic instrument, a non-diagnostic instrument or any other health care instrument. As an example, the laboratory instruments 101 may include, but are not limited to, table top analyzers and standalone analyzers. In some embodiments, user 103 may be a laboratory technician, a visitor or any other person viewing laboratory instruments 101 or present proximate to the laboratory instruments 101.

Figure 1B:
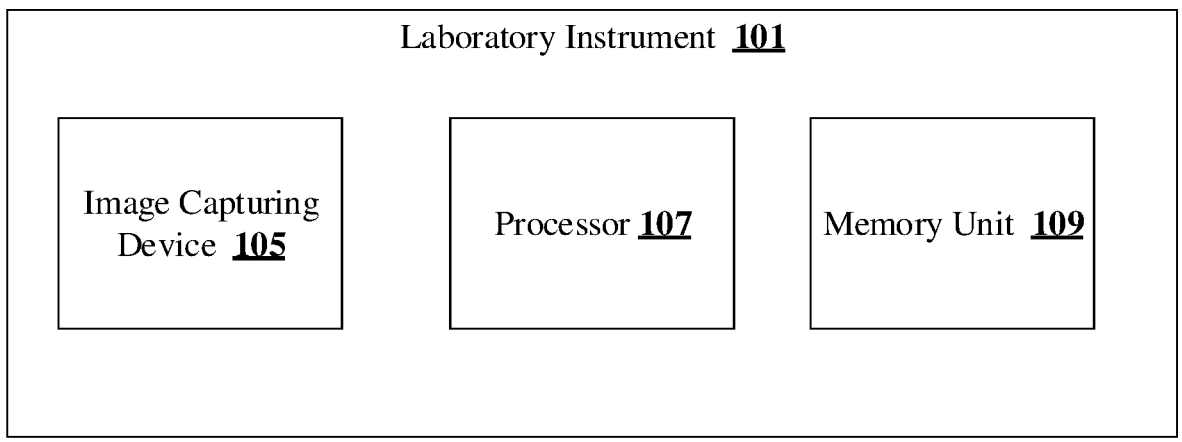
FIG. 1B illustrate an exemplary block diagram of a laboratory instrument in accordance with embodiments of the present disclosure.

Reference is now made to FIG. 1B, which illustrates a block diagram of laboratory instrument 101, which comprises at least one image capturing device 105 (also referred as image capturing device/s 105), a processor 107 and a memory unit 109. In some embodiment, the image capturing device 105 may be coupled with the laboratory instrument 101. The image capturing device 105 is configured to capture at least one image and video during operations of the laboratory instrument 101. As an example, image capturing device 105 may include, but may not be limited to, a camera which may be configured to capture still images periodically or videos continuously. As an example, the camera may be a monochrome camera, a color camera, digital camera and the like. The image capturing device 105 may be configured to capture images of the plurality of objects in the laboratory environment 100. As an example, the plurality of objects may be equipments, region of the equipments, face region of the users 103, Identification (ID) card of the users 103 and the like as shown in FIG. 1A. The processor 107 receives the images of the plurality of objects and detects one or more objects from the images which match with predefined target objects. The predefined target objects and its corresponding one or more features are stored in the memory unit 109.

In some embodiments, the predefined target objects may be defined by the user 103 in real-time. As an example, the predefined target objects may be face region of users 103 in the laboratory environment 100 and a standalone equipment in the laboratory environment 100. The features of the face region and the standalone equipment are extracted and stored in the memory unit 109. As an example, the feature of the face region may be eyes, nose and mouth. As an example, the features of the standalone equipment may be display region, input region and the like.

The image capturing device 105 may capture images of the plurality of objects in the environment. Some of the objects being captured in the images may contain secure data associated with the objects. If the objects being captured match with the predefined objects, the processor 107 may identify such objects as the objects containing secure data and hence mask them to prevent exposure of such data to the outside environment.

In some embodiment, when the one or more objects which match with the predefined objects are identified, the processor 107 may apply a virtual masking object on and around the identified one or more objects to prevent exposure of the secure data associated with the identified one or more objects. In some other embodiments, the virtual masking object may be applied on or around the one or more objects based on the identified one or more objects.

In some embodiments, the predefined target object may be face region of the user 103 which discloses identity of the user 103. The one or more features of the face region may be extracted and stored in the memory unit 109 associated with the processor 107. The image capturing device 105 configured in the laboratory instrument 101 may capture images of the plurality of objects in the laboratory environment 100. The plurality of objects may include face region of the user 103 and one or more equipments. The processor 107 may identify the one or more objects from the images which match with the predefined target objects. The processor 107 may identify the one or more objects based on comparison of one or more features of the one or more objects with features of the target objects using a machine learning technique. If the features of the one or more objects match with the features of the predefined target objects, the processor 107 may identify the one or more objects as matching with the predefined target objects. In this scenario, there may be one or more users 103 in the image captured by the image capturing device 105. The processor 107 may detect face region of the one or more users 103 matching with the predefined target object. The processor 107 may apply the virtual masking object on the face region to prevent exposure of the face region of the user 103 to the outside environment. In some embodiment, the virtual masking object may be an emoticon or any other masking object to mask the face region of the user 103 such that the face region is not exposed to the outside environment which discloses identity of the user 103.

In some embodiment, the predefined target object may be a standalone equipment. The features of the standalone equipment may be extracted and stored in the memory unit 109. The image capturing device 105 configured in the laboratory instrument 101 may capture images of the plurality of objects in the laboratory environment 100. The plurality of objects may include one or more users 103 and one or more equipments. The processor 107 may identify the one or more objects from the images which match with the predefined target objects. The processor 107 may identify the one or more objects based on comparison of one or more features of the one or more objects with features of the target objects using a machine learning technique. If the one or more features of the one or more objects match with the one or more features of the predefined target objects, the processor 107 may identify the one or more objects as matching with the predefined target objects. In this scenario, there may be one or more equipments in the laboratory environment 100. Among the one or more objects, the feature of one of the equipment may match with the features of the predefined target object. The processor 107 identifies one of the one or more objects and applies a virtual masking object around the identified object such that the identified object is not exposed to the outside environment.

As an example, the virtual masking object may be a virtual curtain panel. The virtual curtain panel may be placed at a predefined distance from the image capturing device 105 configured in the laboratory instrument 101. As an example, the predefined distance may be 2 meters from the laboratory instrument 101 configured with the image capturing device 105. The virtual masking object may be placed at 2 meters from the laboratory instrument 101 comprising the image capturing device 105. Once the virtual curtain panel is placed, the view of the identified objects which matches with predefined target objects is blocked for the laboratory instrument 101 comprising the image capturing device 105. This prevents the exposure of the secure data associated with the identified objects to the outside environment.

Figure 2A:
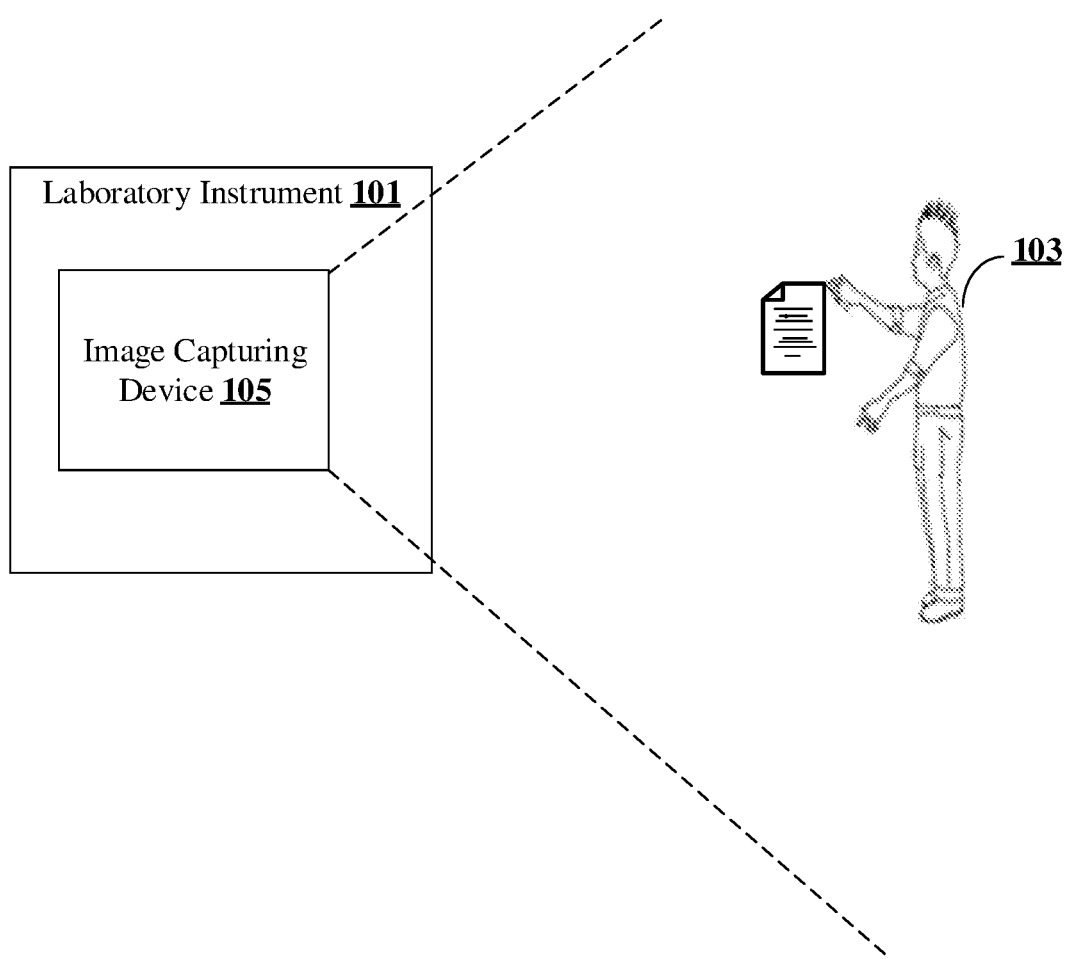
FIG. 2A and FIG. 2B illustrate an exemplary method of applying a virtual masking object on a target object in accordance with an embodiment of the present disclosure.
Figure 2B:
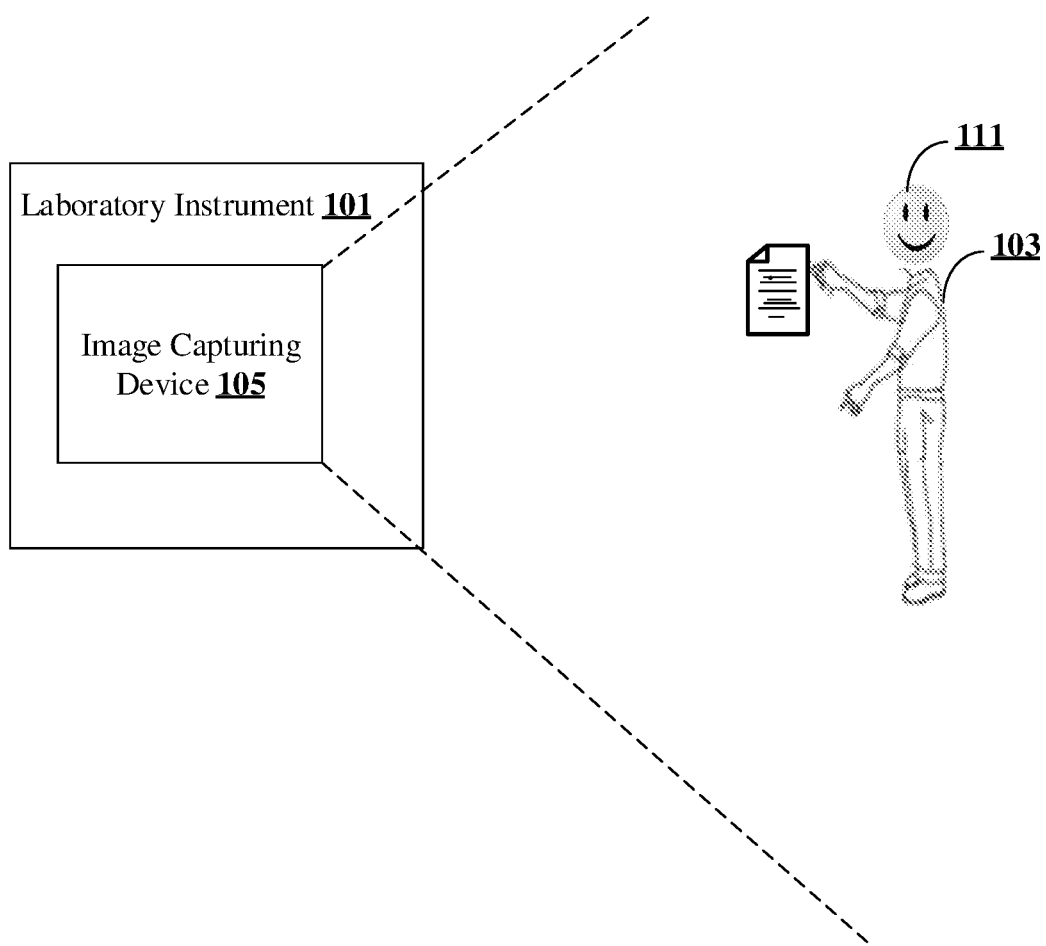

Reference is now made to FIG. 2A that shows an exemplary laboratory environment 100 wherein the user 103 is viewing operation of the laboratory instrument 101. Since the user 103 is viewing the operation of the laboratory instrument 101, user 103 is in the field of view of the image capturing device 105 configured in the laboratory instrument 101. As an example, face region of the user 103 may be configured as a predefined target object. The image capturing device 105 captures the image of the user 103. Since the user face is captured by the image capturing device 105 and it matches with the predefined target object, the processor 107 in the laboratory instrument 101 applies a virtual masking object on the face region such as an emoticon 111 as shown in FIG. 2B such that the emoticon masks or prevents the exposure of the face region of the user 103 to the outside environment through the image capturing device 105.

Figure 3A:
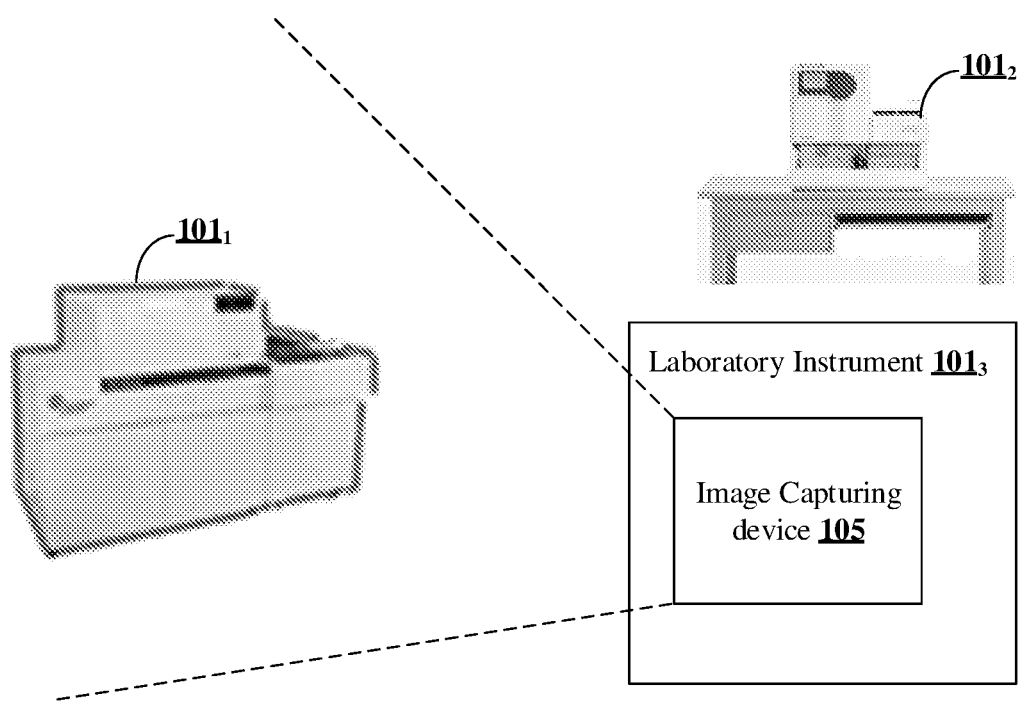
FIG. 3A-FIG. 3D illustrate an exemplary method of applying virtual masking object around the target object in accordance with an embodiment of the present disclosure.
Figure 3B:
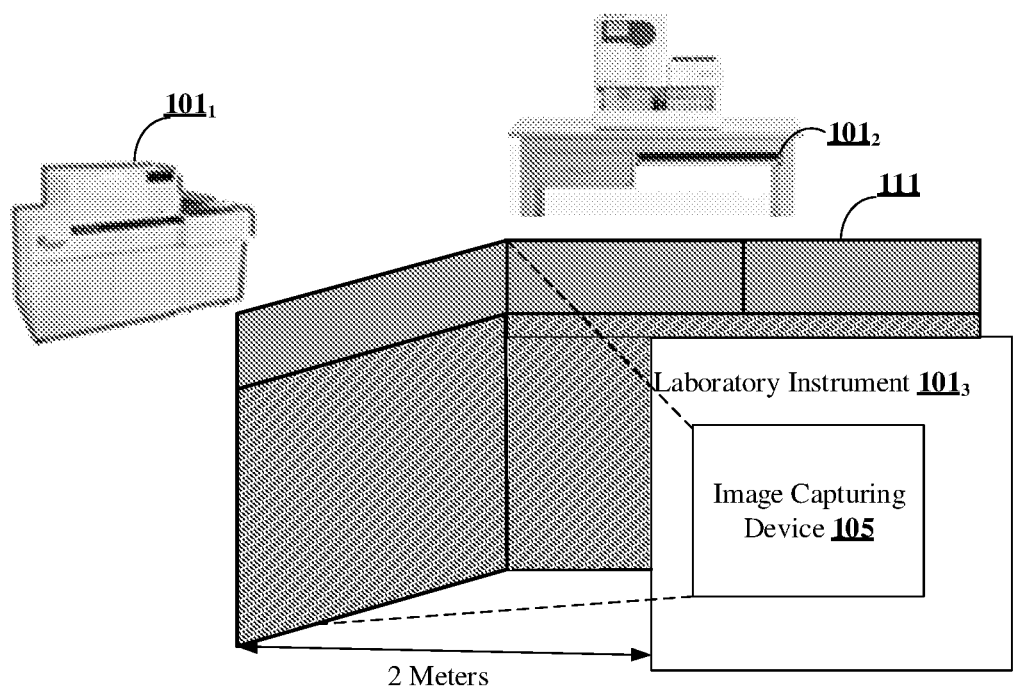

Reference is now made to FIG. 3A that shows an exemplary laboratory environment 100 comprising one or more objects. As an example, image capturing device 105 configured in the laboratory instrument $101_3$ may capture images of plurality of objects in the laboratory environment 100. As an example, image capturing device 105 may capture images comprising two objects such as laboratory instrument 1 $101_1$ which is a standalone device and laboratory instrument 2 $101_2$ is a table top analyzer. The features of the laboratory instrument 1 $101_1$ and the laboratory instrument 2 $101_2$ are extracted and stored in the memory unit 109 associated with a processor 107 configured in the laboratory instrument $101_3$. The predefined target object may be a standalone analyzer. Since the standalone analyzer is predefined as a target object, the data associated with the standalone analyzer consist of security data and hence must be prevented from being exposed to the outside world. In some embodiment, the processor 107 compares the features of all the objects in the images with the features of the predefined target object to identify the object matching with the predefined object using a machine learning technique. In some embodiments, the processor 107 detects the standalone analyzer in the captured image which matches with the predefined target image. Therefore, processor 107 applies a virtual masking object at a predefined distance from the laboratory instrument $101_3$ comprising the image capturing device 105 as shown in FIG. 3B. The virtual masking object applied is an augmented reality based virtual curtain 111 around the laboratory instrument $101_3$. The virtual masking object is applied to mask the view from the image capturing device 105 such that the data associated with the standalone analyzer is prevented from being exposed to the outside world through the image capturing device 105. As an example, the predefined distance may be 2 meters. At 2 meters from the laboratory instrument $101_3$ comprising the image capturing device 105, the virtual curtain 111 may be applied around the laboratory instrument $101_3$ as shown in FIG. 3B such that the standalone analyzer is blocked for view from the image capturing device 105. However, users 103 in the laboratory environment 100 may still view or operate the standalone analyzer. For the purpose of illustration, only side view of the laboratory instrument 101 comprising the image capturing device 105 is blocked which is shown in FIG. 3B. In some other embodiments all sides of the laboratory instrument $101_3$ comprising the image capturing device 105 may be blocked by the virtual curtain 111 (not shown in FIG. 3B).

Figure 3C:
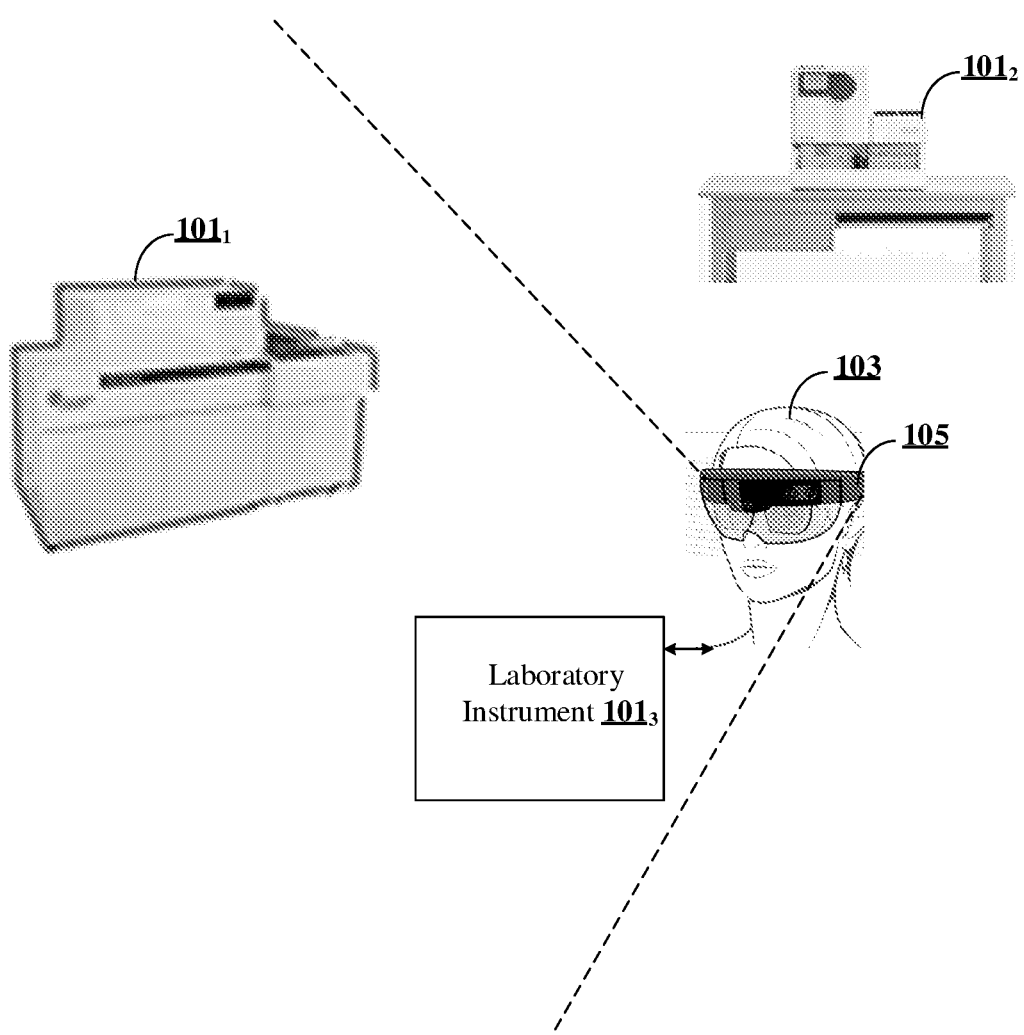
Figure 3D:
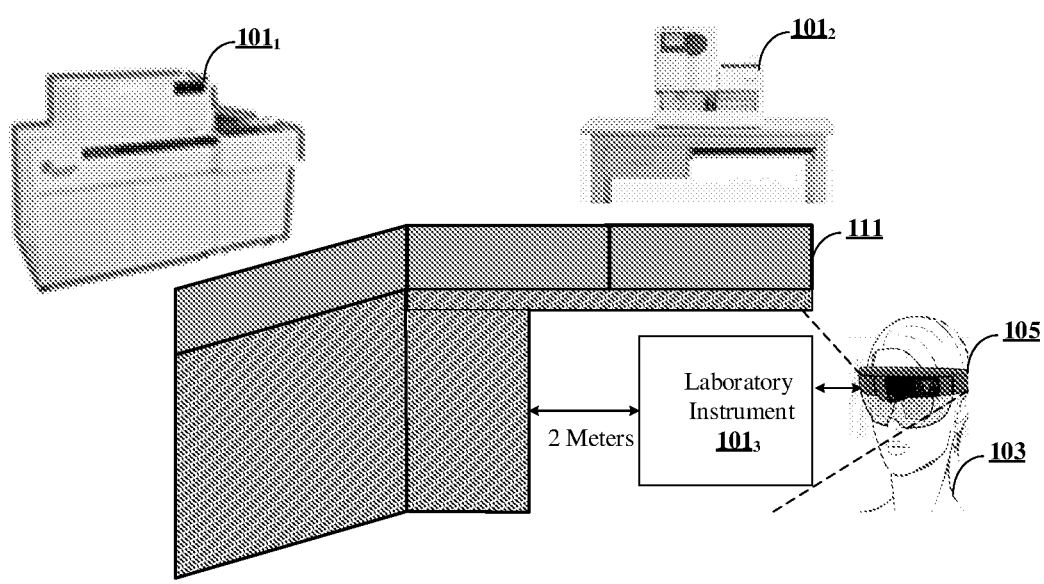

Reference is now made to FIG. 3C that shows an exemplary laboratory environment 100 comprising one or more objects. In some embodiments, image capturing device 105 may be present outside the laboratory instrument $101_3$ as shown in FIG. 3C. The image capturing device 105 present outside the laboratory instrument $101_3$ may represent devices, which includes, but not limited to, Google® glasses worn by a user 103 in the laboratory environment 100. As an example, image capturing device 105 may capture images comprising two objects such as laboratory instrument 1 $101_1$ which is a standalone device and laboratory instrument 2 $101_2$ is a table top analyzer. The features of the laboratory instrument 1 $101_1$ and the laboratory instrument 2 $101_2$ are extracted and stored in the memory unit 109 associated with a processor 107 configured in the laboratory instrument $101_3$. The predefined target object may be a standalone analyzer. Since the standalone analyzer is predefined as a target object, the data associated with the standalone analyzer consist of security data and hence must be prevented from being exposed to the outside world. In some embodiment, the processor 107 compares the features of all the objects in the images with the features of the predefined target object to identify the object matching with the predefined object using a machine learning technique. In some embodiments, the processor 107 detects the standalone analyzer in the captured image which matches with the predefined target image. Therefore, processor 107 applies a virtual masking object at a predefined distance from the laboratory instrument $101_3$ as shown in FIG. 3D. The virtual masking object applied is an augmented reality based virtual curtain 111 around the laboratory instrument $101_3$. The virtual masking object is applied to mask the view from the image capturing device 105 such that the data associated with the standalone analyzer is prevented from being exposed to the outside world through the image capturing device 105. As an example, the predefined distance may be 2 meters. At 2 meters from the laboratory instrument $101_3$, the virtual curtain 111 may be applied as shown in FIG. 3D such that the standalone analyzer is blocked for view from the image capturing device 105.

Figure 4:
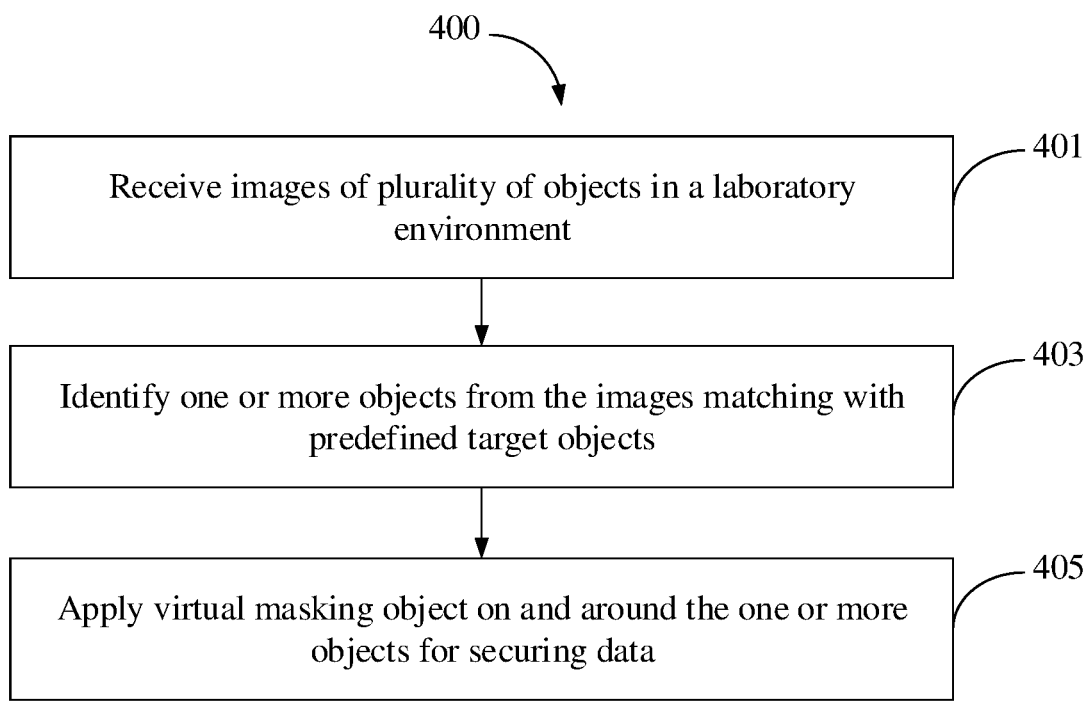
FIG. 4 shows a flowchart illustrating a method for securing data associated with objects captured in a laboratory environment in accordance with an embodiment of the present disclosure.

Reference is now made to FIG. 4 which shows a flowchart illustrating a method for securing data associated with objects captured in a laboratory environment in accordance with some embodiments of the present disclosure.

As illustrated in FIG. 4, method 400 includes one or more blocks illustrating a method for securing data associated with objects in a laboratory environment. Method 400 may be described in the general context of computer executable instructions. Generally, computer executable instructions can include routines, programs, objects, components, data structures, procedures, modules, and functions, which perform functions or implement abstract data types.

The order in which method 400 is described is not intended to be construed as a limitation, and any number of the described method blocks can be combined in any order to implement method 400. Additionally, individual blocks may be deleted from the methods without departing from the spirit and scope of the subject matter described herein. Furthermore, the method 400 can be implemented in any suitable hardware, software, firmware, or combination thereof.

At block 401, method 400 may include receiving, by a processor configured in a laboratory instrument, images of plurality of objects in a laboratory environment. The plurality of objects may include, but not limited to, equipments, region of the equipments, face region of the users and Identification (ID) card of the users. The images may be captured by an image capturing device associated with the laboratory instrument.

At block 403, the method 400 may include identifying, by the processor, from the images, one or more objects matching with predefined target objects. The predefined target objects may be defined by the user in real-time. The predefined target objects are the objects which may include security data and hence must be masked to prevent exposure of the security data to the outside environment.

At block 405, the method 400 may include applying, by the processor, a virtual masking object on and around the one or more objects which matches the predefined target object to secure the data associated with the identified one or more objects. In some other embodiments, the virtual masking object may be applied on or around the one or more objects based on the identified one or more objects. The virtual masking object may be applied on the identified object when the identified object is either face region of a user or ID card of the user. The virtual masking object may be applied around the laboratory instrument comprising the image capturing device when the identified object is equipments or region of the equipments which may comprise secure data.

In an embodiment, the present disclosure discloses a method, system and a laboratory instrument for securing data associated with one or more objects in a laboratory environment. In a further embodiment, the present disclosure provides a method for applying a virtual masking object on or around one or more objects matched with predefined target objects. The virtual masking objects may be placed on the one or more objects when the one or more objects are such as face region of users in the laboratory environment. The virtual masking objects may be placed around the one or more objects when the one or more objects are one or more equipment or region of one or more equipment that must be blocked from the view of the image capturing device. By applying the virtual masking objects on or around the one or more objects, the exposure of the objects to the outside environment is prevented, thereby providing data security.

As described herein a description of an embodiment with several components in communication with each other does not imply that all such components are required. On the contrary a variety of optional components are described to illustrate the wide variety of possible embodiments of the invention.

When a single device or article is described herein, it will be apparent that more than one device/article (whether or not they cooperate) may be used in place of a single device/article. Similarly, where more than one device or article is described herein (whether or not they cooperate), it will be apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the disclosure need not include the device itself.

The specification describes a method, system and laboratory instrument for securing data associated with objects in a laboratory environment. The illustrated steps are set out to explain exemplary embodiments shown, and it should be anticipated that on-going technological development will change the manner in which particular functions are performed. These examples are presented herein for purposes of illustration, and not as a limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present disclosure are intended to be illustrative, but not limiting, of the scope of the disclosure, which is set forth in the following claims.

What is claimed is:

1. A method of securing data associated with objects captured in a specific environment, the method comprising:
   (a) receiving images of a plurality of objects associated with a device;
   (b) identifying, from the images, one or more objects matching with predefined target objects; and
   (c) applying a virtual masking object on the one or more objects matching with the predefined target objects for securing data associated with the one or more matching objects, wherein applying the virtual masking object around the one or more objects is based on a predefined distance around an equipment in the specific environment comprising an image capturing device configured to capture the images of the plurality of objects in the specific environment, and comprises:
      (j) one or more acts selected from:
         (A) identifying the predefined distance; and
         (B) marking the predefined distance by a user in real time; and
      (ii) applying the virtual masking object at the predefined distance from the image capturing device.

2. The method of claim 1, wherein the device is configured to allow a user to mark the plurality of objects dynamically in real time.

3. The method of claim 1, wherein applying the virtual masking object around the one or more objects comprises identifying the predefined distance.

4. The method of claim 1, wherein applying the virtual masking object around the one or more objects comprises marking the predefined distance in real time by the user.

5. The method of claim 1, wherein the one or more objects comprises at least one of:
   (a) a face region of one or more personnel in the specific environment;
   (b) an identification (ID) card of the one or more personnel in the specific environment;
   (c) an item of equipment in the specific environment; and
   (d) one or more regions of the item of equipment.

6. The method of claim 1, wherein the one or more objects matching with the predefined target objects are identified based on processing of the one or more objects using a machine learning technique.

7. The method of claim 1, wherein the specific environment is a laboratory environment, and wherein the device is a laboratory instrument.

8. A system for securing data associated with objects captured in a specific environment, the system comprising:
   (a) a processor; and
   (b) a memory unit communicatively coupled to the processor, wherein the memory unit stores processor-executable instructions, which, on execution, cause the processor to perform a method comprising:
      (i) receiving images of a plurality of objects, associated with a device;
      (ii) identifying, from the images, one or more objects matching with predefined target objects; and
      (iii) applying a virtual masking object on the one or more objects matching with the predefined target objects for securing data associated with the one or more matching objects, wherein the instructions comprise instructions to cause the processor to apply the virtual masking object around the one or more objects based on a predefined distance around an equipment in the specific environment comprising an image capturing device configured to capture the images of the plurality of objects in the specific environment, and wherein applying the virtual masking object comprises:
         (A) one or more acts selected from:
            (I) identifying the predefined distance; and
            (II) obtaining the predefined distance from a user in real time; and
         (B) applying the virtual masking object at the predefined distance from the image capturing device.

9. The system of claim 8, wherein the processor configured to allow a user to mark the plurality of objects dynamically in real time.

10. The system of claim 8, wherein applying the virtual masking object around the one or more objects comprises identifying the predefined distance.

11. The system of claim 8, wherein applying the virtual masking object around the one or more objects comprises obtaining the predefined distance from the user in real time.

12. The system of claim 8, wherein the one or more objects comprises at least one of:
   (a) a face region of one or more personnel in the specific environment;
   (b) an identification (ID) card of the one or more personnel in the specific environment;
   (c) an item of equipment in the specific environment; and
   (d) one or more regions of the item of equipment.

13. The system of claim 8, wherein the one or more objects matching with the predefined target objects are identified based on processing of the one or more objects using a machine learning technique.

14. A non-transitory computer readable medium having stored thereon instructions which, on execution, cause a processor to perform a method comprising:
   (a) receiving images of a plurality of objects, associated with a device;
   (b) identifying, from the images, one or more objects matching with predefined target objects; and
   (c) applying a virtual masking object on the one or more objects matching with the predefined target objects for securing data associated with the one or more matching objects, wherein the instructions comprise instructions to cause the processor to apply the virtual masking object around the one or more objects based on a predefined distance around an equipment in the specific environment comprising an image capturing device configured to capture the images of the plurality of objects in the specific environment, and wherein applying the virtual masking object comprises:
(i) one or more acts selected from:
(A) identifying the predefined distance; and
(B) obtaining the predefined distance from a user in real time; and
(ii) applying the virtual masking object at the predefined distance from the image capturing device.

15. The medium of claim 14, wherein the instructions are further operable to configure the processor to allow a user to mark the plurality of objects dynamically in real time.

16. The medium of claim 14, wherein applying the virtual masking object around the one or more objects comprises identifying the predefined distance.

17. The medium of claim 14, wherein applying the virtual masking object around the one or more objects comprises obtaining the predefined distance from the user in real time.

18. The medium of claim 14, wherein the one or more objects comprises at least one of:
(a) a face region of one or more personnel in the specific environment;
(b) an identification (ID) card of the one or more personnel in the specific environment;
(c) an item of equipment in the specific environment; and
(d) one or more regions of the item of equipment.

19. The medium of claim 14, wherein the one or more objects matching with the predefined target objects are identified based on processing of the one or more objects using a machine learning technique.

* * * * *